(12) United States Patent
Smet et al.

(10) Patent No.: US 7,744,938 B2
(45) Date of Patent: Jun. 29, 2010

(54) YEAST PACKAGING

(75) Inventors: Peter René Anna Smet, Sint Niklaas (BE); Karel Alfons Frans Blomme, Evergem (BE); Gabriel Petrus Van Eetvelde, Evergem (BE)

(73) Assignee: LeSaffre et Compagnie, Paris (FR)

( * ) Notice: Subject to any disclaimer, the term of this patent is extended or adjusted under 35 U.S.C. 154(b) by 1267 days.

(21) Appl. No.: 10/552,630

(22) PCT Filed: Apr. 13, 2004

(86) PCT No.: PCT/EP2004/003890

§ 371 (c)(1),
(2), (4) Date: Oct. 7, 2005

(87) PCT Pub. No.: WO2004/090116

PCT Pub. Date: Oct. 21, 2004

(65) Prior Publication Data

US 2006/0193948 A1    Aug. 31, 2006

(30) Foreign Application Priority Data

Apr. 10, 2003 (EP) .................................. 03008349
Dec. 23, 2003 (EP) .................................. 03029589

(51) Int. Cl.
*C12N 1/18* (2006.01)
*A21D 8/04* (2006.01)

(52) U.S. Cl. .................... 426/62; 426/61; 426/285; 426/106; 426/561; 426/656

(58) Field of Classification Search .................... 426/61, 426/62, 561, 656
See application file for complete search history.

(56) References Cited

U.S. PATENT DOCUMENTS

| | | | | |
|---|---|---|---|---|
| 3,615,685 A | * | 10/1971 | Fantozzi et al. | 426/62 |
| 4,318,930 A | * | 3/1982 | Clement et al. | 426/62 |
| 4,318,991 A | * | 3/1982 | Hill | 435/245 |
| 4,450,153 A | * | 5/1984 | Hopkins | 424/94.4 |
| 5,716,654 A | * | 2/1998 | Groenendaal | 426/62 |
| 6,284,244 B1 | * | 9/2001 | Owades | 424/93.51 |
| 6,306,391 B1 | | 10/2001 | Modi et al. | |
| 6,383,530 B1 | * | 5/2002 | Iwashita et al. | 426/19 |

FOREIGN PATENT DOCUMENTS

| | | | |
|---|---|---|---|
| EP | 1213347 A1 | * | 6/2002 |
| EP | 1 247 642 A2 | | 10/2002 |
| WO | WO 97/04037 | * | 3/1992 |
| WO | WO 94/14151 A1 | | 6/1994 |
| WO | WO 95/25436 A1 | | 9/1995 |

OTHER PUBLICATIONS

Burrows et al., "Routine method for determination of the activity of Baker's Yeast," Reprinted from the Journal of the Institute of Brewing, vol. LXV, No. 1 (vol. LVI, New Series), Jan.-Feb. 1959, pp. 39-45.

Godon et al., "Guide Pratique d'Analyses dans les Industries des Cereales," Tec. & Doc. 1997, ISBN 2-7430-0123-2, $2^{nd}$ Edition, pp. 579-584 and 680-681.

Reed et al., Yeast Technology, $2^{nd}$ Edition, 1991 (ISBN 442-31892-8), pp. 297-307.

Scevola, et al., Acid Tolerance and Fecal Recovery Following Oral Administration of *Saccharomyces cerevisiae*; Journal of Chemotherapy, vol. 15, No. 2 (143-147), 2003.

* cited by examiner

*Primary Examiner*—Jennifer McNeil
*Assistant Examiner*—Dominique Womack
(74) *Attorney, Agent, or Firm*—Foley & Lardner LLP

(57) ABSTRACT

The invention relates to active dry yeast which is packed in the form of a fermentation agent as a tablet containing active dry yeast.

24 Claims, No Drawings

YEAST PACKAGING

The present invention relates to a form of active dry yeast packaging, and in particular, to a form of active dry baker's yeast packaging.

Baker's yeast is marketed in liquid form, semi-moist form, and dry form.

Liquid yeast or cream yeast can be preserved up to 28 days if it is maintained at a temperature between 0 and 7° C.

Crumbled yeast and yeast pressed into blocks—semi-moist yeasts—can be preserved up to 31 days, if they are maintained at a temperature between 0 and 10° C.

Active dry yeast, instant or not instant, in powder, in vermicelli, spheroids, or fine granules, can be preserved for at least 2 years at ambient atmosphere (20 to 25° C.) if it is protected against moisture, in particular moisture in the ambient environment, and preferably against oxygen and light.

The fact that active dry yeast can be preserved at ambient temperature for a much longer period than liquid yeast, yeast cream, and instant or crumbled yeast is one of the principal advantages of active dry yeast. Its long shelf life makes in particular active dry yeast the form of baker's yeast preferred by the users who, as do homebakers, only occasionally need a small quantity of baker's yeast.

As mentioned above, conserving active dry yeast for several months, especially in the form of instant dry yeast, requires that it is stored safe from moisture and oxygen.

This is currently carried out by packaging the powder, vermicelli, or fine granules of instant active dry yeast in airtight bags, small pouches, or sachets which are either vacuum sealed or under an artificial dry atmosphere such as nitrogen atmosphere, for example.

In order to enable the proper storage of active dry yeast, the material of the aforesaid bags, small pouches, or sachets must fulfill the following minimal requirements:

the material must first, quite obviously, be highly airtight sealed against moisture and oxygen,
the material must be appropriate for foodstuffs,
the material must be supple and pliable and resist perforation and tearing, and
the material must be weldable and yield a solid, airtight weld.

Preferably, the material must be opaque so as to protect the dry active yeast from the harmful effects of light.

Currently, instant active dry yeast is packaged in bags, small pouches, or sachets made of multi-layer opaque material, containing at least one metallic or metallized layer, of high quality and price, such as that described on pages 306-307 of the reference book "Yeast Technology" by Reed and Nagodawithana, second edition 1991 (ISBN 0-442-31892-8).

The conservation results obtained with such bags, small pouches, and sachets has proven in general to be positive.

A problem arises however concerning the packaging of small quantities of active dry yeast, such as for example of active dry yeast amounts of 25 grams or less, and in particular with regard to the packaging of an amount of active dry yeast that corresponds to the quantity necessary for the preparation of a single loaf of bread or similar product. Indeed, in this case, the price of the packaging is equivalent or exceeds the price of manufacturing the small quantity or amount of active dry yeast, if not being a multiple.

The goal of the present invention is to fulfill an alternative packaging for active dry yeast.

The present invention relates to a fermentation agent containing active dry yeast, the aforementioned fermentation agent being in tablet form.

Among active dry yeasts, instant active dry yeast for breadmaking and non-instant active dry yeast for breadmaking are distinguished. Instant active dry yeast (IADY or IDY) is distinguished in particular from non-instant active dry yeast (ADY), by the fact that, in order to have an increased activity, the non-instant active dry yeast must be rehydrated before its introduction into the bread dough, whereas the instant active dry yeast is a fermentation agent which does not require such rehydration (see, for example, pages 297-304 of the reference work "Yeast Technology" by Reed and Nagodawithana, second edition 1991 [ISBN 0-442-31892-8]).

As used in this context, the term "tablet" refers to a compact solid mass of unspecified form. The tablet according to the invention can be obtained by casting and/or compression in a mold, by granulation, agglomeration, or other known processes, in particular pharmaceutical processes, for the preparation of tablets, pills, etc.

The fermentation agent according to the invention has a dry matter content of at least 88%, preferably from 88 to 98% by weight, preferably still of at least 90% by weight, and more preferably from 90 to 98% by weight, and more preferably still from 93 to 96% by weight.

The mass of the tablet can vary from 1.0 g to 250.0 g.

According to one embodiment, the fermentation agent presents a dry matter content from 90 to 96% by weight. In this case, the fermentation agent typically contains non-instant active dry yeast.

According to a second embodiment, the fermentation agent presents a dry matter content from 94 to 97% by weight. In this case, the fermentation agent typically contains instant active dry yeast.

In an advantageous way, the equivalent of 160 mg dry matter of the fermentation agent, i.e. the tablet, yields in test A1 described below a production of $CO_2$ in 2 hours of 20 to 150 ml, preferably of 30 to 130 ml, and preferably still of 40 to 120 ml, and according to a form particularly preferred of 90 ml to 170 ml.

In a useful way, the equivalent of 160 mg dry matter of the fermentation agent, i.e. the tablet, yields in test A2 described below a production of $CO_2$ in 2 hours of 15 to 120 ml, preferably of 25 to 110 ml, and preferably still of 35 to 100 ml, and according to a form particularly preferred of 90 ml to 170 ml. In particular, the equivalent of 160 mg dry matter of the fermentation agent can yield, in tests A1 and A2, a production of $CO_2$ in two hours of 20 to 150 ml, preferably of 30 to 130 ml, and preferably still of 40 to 120 ml, and according to a form particularly preferred of 90 ml to 170 ml.

The quantity of $CO_2$ produced by the fermentation agent in tests A1 and A2 will depend in particular on the yeast strain present, on the process of obtaining the yeast, on the nature and quantities of the other ingredients possibly present in or on the tablet, and on the compacting process used.

In a preferred way, the fermentation agent presents a high production of $CO_2$ in test A1 and/or test A2. However, lower productions of $CO_2$ are perfectly acceptable, as in particular the productions of $CO_2$ in 2 hours in test A1 greater than or equal to 20 ml, but lower than or equal to 85 ml, lower than or equal to 75 ml, or lower than or equal to 60 ml, and/or the productions of $CO_2$ in 2 hours in test A2 greater than or equal to 15 ml, but lower than or equal to 75 ml, lower than or equal to 65 ml, or lower than or equal to 55 ml.

The weight of the tablet can vary, in particular according to the use or envisaged market. The weight of a tablet is typically at least 1.5 g, at least 2.0 g, at least 2.5 g, or at least 3.0 g. The fermentation agent according to the invention can thus be in a tablet form from 1.0 to 100.0 g; from 1.5 to 50.0 g; from 2.0 to 12.0 g; or from 2.0 to 5.0 g.

The active dry yeast content of the fermentation agent according to the invention can also vary. Thus, the fermentation agent will typically consist of at least 30% active dry yeast by weight. In a useful way, the fermentation agent can consist of at least 50% by weight, preferably of at least 75% by weight, preferably still of at least 80% by weight, and more preferably still of at least 90% active dry yeast by weight.

Apart from the active dry yeast, the fermentation agent according to the invention can also include other ingredients.

Thus, the fermentation agent can advantageously include one or more useful auxiliary technological means useful for drying yeast and/or which have a role as improver in breadmaking. The fermentation agent can in particular include one or more breadmaking improvers from the group of antioxidant agents, for example ascorbic acid, from the group of reducing agents, for example L-cysteine, from the enzymes, from emulsifiers, for example from sorbitan esters, from the gluten. In particular, the fermentation agent can include one or more bread improvers belonging to the group comprising ascorbic acid, enzymes, cysteine, gluten, malts and malt extracts, yeast extracts and inactive dry yeasts. When the fermentation agent includes one or more enzymatic bread improvers, it preferentially includes one or more enzymes of the group of α-amylases, proteases, xylanases and pentosanases, amyloglucosidases, glucose oxydases, lipases, and phospholipases.

The fermentation agent according to the invention includes in a useful way one or more emulsifiers, in particular emulsifiers from the following group: lecithin, fatty acid monoglycerides and diglycerides, diacetyl tartaric acid esters of monoglycerides and diglycerides (DATEM), polyglycerol esters, sorbitan esters, and the stearoyl-lactylates.

The fermentation agent according to the invention can also include one or more excipients. In this context, the term "excipient" refers to substances which, because of their nature or their quantity, act neither as a fermentation agent nor as a bread improver, but which facilitate, for example, the preparation, shaping, or conservation of the fermentation agent. The fermentation agent can thus include one or more excipients such as:

polysaccharides (such as, for example, cellulose, and in particular microcrystalline cellulose),
cellulose derivatives (such as, for example, methyl cellulose and carboxymethyl cellulose),
gums,
pectins,
monosaccharides (such as, for example, fructose and glucose),
disaccharides (such as, for example, lactoses such as monohydrated α-lactose, anhydrous β-lactose, and sucrose),
polyalcohols (such as, for example, xylitol, mannitol, sorbitol, glycerol),
calcium (di)phosphate,
polyvinylpyrrolidone.

Monosaccharides, notably glucose, and in particular fructose, are preferred excipients.

According to one embodiment, the fermentation agent includes, as an excipient, one or more effervescent agents. The presence of such effervescent agents facilitates the disintegration of the fermentation agent in the dough or, if need be, the fermentation agent resuspension before its introduction into the dough. Effervescent agents suitable for the present invention are, for example, sodium bicarbonate possibly in combination with citric acid, lactic acid, and/or tartaric acid. Other effervescent agents appropriate for foodstuffs can also be used. Preferably, if the effervescent agents create a gas release measured in tests A1 or A2, this gas release due to the effervescent agents will be less than 50% of the total gas release measured in tests A1 or A2.

The fermentation agent resuspension before its introduction into the dough improves and/or facilitates the good distribution of the aforesaid agent in the bread dough.

The fermentation agent according to the invention can possibly include nutritional supplements such as iodine, one or more vitamins, fluorine, mineral food supplements, tocopherols, trace elements, omega-3 fatty acids, nutritional fibers, or still yet flour, honey, cane molasses, etc; taste improvers such as salt substitutes, sweeteners, spices; natural or synthetic flavors, such as vanilla, orange blossom, rum, red fruits, citrus fruits; preservatives, such as propionates; and/or dyes for the dough and/or for the baked product, such as caramel; knowing that certain ingredients can have multiple effects.

In an advantageous way, the fermentation agent is in the form of a tablet covered by a layer that forms a barrier against moisture and/or oxygen, i.e. a barrier against moisture and/or atmospheric oxygen.

For example, this barrier against moisture and/or oxygen can be a layer of one or more emulsifiers and/or one or more fats for coating the interior of the tablet which includes the active dry yeast. This external layer can include auxiliary technological means having a role as bread improvers.

It should be noted that during the end use of the fermentation agent, a distribution as homogeneous as possible of yeast in the dough is sought, which implies the disintegration of the tablet before the preparation of the dough or during kneading. Disintegration of the tablet before the preparation of the dough can be, for example, a mechanical disintegration, for example between the fingers or the hands, or a disintegration by rehydration or resuspension.

In the case of a tablet covered by a layer that forms a barrier against moisture and/or oxygen, the material of the layer must thus allow such a disintegration of the tablet. The layer that forms a barrier against moisture and/or oxygen can thus be in a material that allows the layer to disintegrate during the kneading of the dough or that allows the layer to disintegrate or dissolve in the water present in the dough.

It is also possible to incorporate such a material in the mass of the fermentation agent, so that the active dry yeast is surrounded by material that forms a barrier inside the tablet against moisture and/or oxygen.

Many coating materials that are suitable as a layer forming a barrier against moisture and/or oxygen for the tablets according to the invention and many useful coating processes are known particularly in the sugar refining and medicine industries. In practice, the coating materials used are those which do not become sticky at the temperatures encountered during the transport and storage of the fermentation agents.

The purpose of the barrier against moisture and/or oxygen is to reduce the direct contact between the fermentation agent on the one hand, in particular the active dry yeast which it contains, and on the other hand the moisture and/or oxygen in the gas atmosphere surrounding the tablet. It is thus not essential that this barrier is completely impermeable to moisture and/or oxygen in the atmosphere. In practice, a barrier with limited permeability that considerably delays the diffusion of oxygen and/or water molecules through the barrier can be sufficient.

The fermentation agent according to the invention can also be in tablet form provided with one or more scoring marks which facilitate its division into several portions.

It is possible to incorporate the agent according to the invention into a bread flour or into a mixture, such as, for example, a pizza or waffle mix, that contains the bread flour and other ingredients, such as, in particular, bread improvers.

As indicated above, the capacity of the fermentation agent according to the invention to produce $CO_2$ can be evaluated by tests A1 and A2 below. Test A1 makes use of an unsweetened flour-based medium, and test A2 makes use of a lightly sweetened flour-based medium.

Test A1

The volume of $CO_2$ released by the fermentation agent according to the invention is measured with a Burrows and Harrison fermentometer by the method for measuring the volume of $CO_2$ released by yeast described on pages 579 to 584 of the reference book "The practical guide to analyses in the cereal industry" coordinated by B. Godon and W. Loisel—Edited by Lavoisier—Tec & Doc—1997—ISBN 2-7430-0123-2—Second edition—by using the procedure for dried yeasts with rehydration of the fermentation agent at 38° C.

The flour is a whole wheat flour with a Hagberg fall index of 200 to 300 seconds (as defined on pages 680 and 681 of the aforesaid reference book "The practical guide to analyses in the cereal industry").

The quantity of 160 mg dry matter of the fermentation agent corresponds to the quantity of dry matter of the fermentation agent present in the 15 ml taken from the aqueous suspension necessary for kneading (1.066 g×15 ml/100 ml) (see page 583 of the aforesaid reference book "The practical guide to analyses in the cereal industry").

Test A2

The volume of $CO_2$ released by the fermentation agent is measured with a Burrows and Harrison fermentometer by the method described on pages 579 to 584 of the reference book "The practical guide to analyses in the cereal industry" mentioned above, by using the procedure for dried yeasts with rehydration of the fermentation agent at 38° C. mentioned above, with the following modification: before incubation of the 20 g batches of whole wheat flour, 2 g of sucrose is decanted into the tubes.

The present invention also relates to processes for the production of a fermentation agent in tablet form, the aforementioned fermentation agent having a dry matter content of at least 88% by weight, preferably of at least 90% by weight, and preferably still of at least 93% by weight, and even more preferably of at least 94% by weight, and containing active dry yeast, as well as the fermentation agents thus obtained.

The invention relates, for example, to a process in which the tablet is formed by compaction. The compaction pressure can vary. It can, for example, being less than $3×10^8$ Pa, preferably from $0.5×10^5$ to $1×10^8$ Pa, and preferably still from $0.5×10^5$ to $5×10^7$ Pa.

In a useful way, the process includes the preparation of a mixture having a dry matter content of at least 88% by weight, preferably of at least 90% by weight, preferably still of at least 93% by weight, and more preferably still of at least 94% by weight, and containing active dry yeast, and the formation of a tablet of the aforementioned mixture, and in particular the formation of a tablet by compaction of the aforementioned mixture with a compaction pressure as defined above. The aforementioned active dry yeast can be an instant and/or a non-instant active dry yeast.

In an advantageous way, in the process above, the mixture containing active dry yeast is fulfilled by spraying an excipient, for example containing a monosaccharide, on the active dry yeast, with the active dry yeast, being maintained for example in a fluidized bed during this spraying.

Processes, such as described above, have proven to be particularly interesting for the production of fermentation agents according to the invention, such as those defined above.

The present invention also encompasses the use of a fermentation agent according to the invention in the preparation of a dough for a baked product.

The invention also relates to processes for the preparation of a dough for a baked product, a process that includes a step of mixing the fermentation agent according to the invention with the other dough ingredients, such as flour, in particular. The fermentation agent can be mixed as such with other dough ingredients, and can be disintegrated mechanically (manually, for example) before being mixed with other dough ingredients or can be rehydrated before being mixed with other ingredients.

The invention also relates to processes for the preparation of baked products, processes which include a step of preparing a dough as described above, a step of fermenting the dough by the fermentation agent, and a step of baking the fermented dough thus obtained.

The doughs are, for example, doughs for bakery goods, in particular for breads, pastries, sweet breads, pizzas, crepes, waffles, etc.

The present invention also relates to an active dry yeast packaging which includes one or more tablets of this fermentation agent.

The agent according to the invention can be packaged in various packaging, such as containers, preferably made of plastic, envelopes, etc.

According to one embodiment of the packaging according to the invention, the one or more tablets are individually wrapped in a layer that forms a barrier against moisture and preferably against oxygen. Two or three or more tablets can also be wrapped together in a layer that forms a barrier against moisture and preferably against oxygen.

The layer that forms a barrier against moisture and preferably against oxygen is preferably opaque.

Suitable layers that form a barrier against moisture and preferably against oxygen are known and are, for example, described in documents WO-A-94/14151 and WO-A-95/25436.

According to one form of practical implementation, the packaging includes tablets which are from larger sheets of identical form, size, and substance, understanding that a sheet is a flattened tablet. Preferably, in the packaging a series of these tablets is aligned resting one against the other, with the entire series being wrapped in a cylindrical envelope.

It should be noted that, in the present text, the term cylindrical is used in the broad sense. This term thus refers not only to cylinders having a circular cross section, but also to cylinders having a different cross section, such as, for example, a polygonal cross section, such as a triangular, square, rectangular, hexagonal, or octagonal section. The cylindrical envelope can thus be a parallelepipedic envelope. The tablets are of a form suitable to the aforementioned envelopes.

This cylindrical envelope is advantageously an envelope that forms a barrier against moisture and preferably against oxygen.

This cylindrical envelope can be a flexible sheet that envelops the entire series.

The aforementioned flexible sheet can, for example, be a sheet that forms a barrier against moisture and preferably against oxygen as described in documents WO-A-94/14151 and WO-A-95/25436 cited above, or also a sheet that forms a barrier against moisture and preferably against oxygen as described in document EP-A-1247642.

Packaging according to the invention can also be a tube, typically made of plastic or of another rigid material, provided with a stopper, tubes in which several tablets are stored. The tube can, in a useful way, also be provided with a desiccation element. Such tubes provided with a stopper and such desiccation element are known in the field of pharmacy in particular. The tube is preferably opaque.

Packaging according to the invention can also include a sachet containing one or more tablets. The aforementioned sachet is preferably formed of a material that forms a barrier against moisture and preferably against oxygen, and is also preferably opaque.

Packaging according to the invention can also include a blister sheet containing several tablets.

The fermentation agent according to the invention and its packaging are in particular useful as a fermentation agent for household use. However, the fermentation agent according to the invention and its packaging can also be used in other application fields. Thus, the fermentation agent and/or packaging can be part of a unit that contains flour or a mixture that contains flour, such as, for example, a mix for waffles, and the fermentation agent.

EXAMPLE

A homogeneous mixture is prepared with the following ingredients:

100 parts in weight of instant active dry baker's yeast,
1 part in weight of glycerol,
5 parts in weight of sodium bicarbonate as an effervescent agent,
5 parts in weight of citric acid.

Pastilles of a diameter of 2 cm and a weight of 2.22 g are prepared by compaction under a pressure of 223 kg/cm$^2$ ($2 \times 10^7$ Pa). Each pastille contains a quantity of the mixture which corresponds to 2 g of instant dry yeast.

A bread dough is prepared with the following ingredients:
1800 g of whole wheat flour,
1060 g of water,
36 g of table salt,
18 g of standard bread improver,
10 pastilles.

The dough is kneaded in an OASE® Spiralkneter SPK8 kneading machine manufactured by DIOSNA (Osnabrück, Germany) at the initial speed for 3 minutes, then at the second speed until the temperature in the dough reaches 26° C.

The dough is divided into three dough rolls of 900 g each.

The dough rolls are formed into dough balls which are allowed to rest for 30 minutes (the first fermentation).

The dough balls are then elongated and allowed to rest (the second fermentation) until obtaining the desired volume.

After the second fermentation, the dough rolls are placed in the oven and baked at 200° C. for 35 minutes.

The baked breads have the appearance (volume, color, structure) and the organoleptic properties of an analogous bread prepared with traditional instant active yeast dry. No rheological problems appeared during the preparation of the dough.

The invention claimed is:

1. A fermentation agent tablet comprising active dry yeast, wherein a dry matter content of the tablet is at least 88% by weight, wherein the tablet weighs from 1.0 g to 250.0 g, wherein the tablet further comprises at least one breadmaking improver, and wherein at least 50% by weight of the tablet is the active dry yeast.

2. The tablet of claim 1, wherein the dry matter content of the tablet is from 90% to 96% by weight and wherein the active dry yeast comprises non-instant active dry yeast.

3. The tablet of claim 1, wherein the dry matter content of the tablet is from 94% to 97% by weight and wherein the active dry yeast comprises instant active dry yeast.

4. The tablet of claim 1, wherein 160 mg of the dry matter of the tablet is capable of producing from 20 to 150 ml of $CO_2$ in 2 hours in Test A1.

5. The tablet of claim 1, wherein 160 mg of the dry matter of the tablet is capable of producing from 20 to 150 ml of $CO_2$ in 2 hours in Tests A1 and A2.

6. The tablet of claim 1, wherein 160 mg of the dry matter of the tablet is capable of producing from 15 to 120 ml of $CO_2$ in 2 hours in Test A2.

7. The tablet of claim 1, wherein the tablet weighs from 1.0 to 100.0 g.

8. The tablet of claim 1, wherein at least 75% by weight of the tablet is the active dry yeast.

9. The tablet of claim 1, wherein the tablet further comprises at least one ingredient for drying yeast.

10. The tablet of claim 9, wherein the breadmaking improver is selected from the group consisting of antioxidant agents, reducing agents, enzymes and emulsifiers.

11. The tablet of claim 1, wherein the tablet further comprises at least one excipient.

12. The tablet of claim 11, wherein the excipient is selected from the group consisting of polysaccharides, cellulose derivatives, gums, pectins, monosaccharides, disaccharides, calcium phosphate, calcium diphosphate, polyvinylpyrrolidone and polyalcohols.

13. The tablet of claim 1, wherein the tablet further comprises monosaccharide selected from the group consisting of fructose and glucose.

14. The tablet of claim 1 further comprising a covering layer, wherein the covering layer forms a barrier against moisture, oxygen or a combination thereof.

15. A method comprising preparing a dough for a baked product using the fermentation agent tablet of claim 1.

16. A method of preparing a dough for a baked product comprising mixing the fermentation agent tablet of claim 1 with dough ingredients.

17. The method of claim 16, further comprising fermenting the dough by the fermentation agent tablet and baking the fermented dough.

18. A packaging for active dry yeast, the packaging comprising at least one of the tablets of claim 1.

19. The packaging of claim 18, comprising one or more envelopes, wherein each of the envelopes contains one or more of the tablets and wherein each of the envelopes forms a barrier against moisture, oxygen or a combination thereof.

20. The packaging of claim 18, wherein the tablets are identical in form, shape and substance and wherein the packaging comprises a series of aligned sheets resting against each other, and wherein the series are wrapped in a cylindrical envelope.

21. The packaging of claim 20, wherein the cylindrical envelope forms a baffler against moisture, oxygen or a combination thereof.

22. The packaging of claim 20, wherein the cylindrical envelope is a flexible sheet.

23. The packaging of claim 18 further comprising a tube with a stopper, wherein the tube contains two or more of the tablets.

24. The packaging of claim 18 further comprising a sachet containing one or more of the tablets or a blister sheet containing two or more of the tablets.

* * * * *

UNITED STATES PATENT AND TRADEMARK OFFICE
CERTIFICATE OF CORRECTION

PATENT NO. : 7,744,938 B2  
APPLICATION NO. : 10/552630  
DATED : June 29, 2010  
INVENTOR(S) : Peter René Anna Smet et al.

Page 1 of 1

It is certified that error appears in the above-identified patent and that said Letters Patent is hereby corrected as shown below:

IN THE CLAIMS

Claim 21, Column 8, Line 52, please replace "envelope forms a baffler against moisture" with -- envelope forms a barrier against moisture --.

Signed and Sealed this
Twenty-third Day of August, 2011

David J. Kappos
*Director of the United States Patent and Trademark Office*